US006144444A

United States Patent [19]

Haworth et al.

[11] Patent Number: 6,144,444

[45] Date of Patent: Nov. 7, 2000

[54] APPARATUS AND METHOD TO DETERMINE BLOOD PARAMETERS

[75] Inventors: William S. Haworth, Glasgow, United Kingdom; Mark S. Goodin, Solon, Ohio; Mark A. Thompson, Savage, Minn.

[73] Assignee: Medtronic Avecor Cardiovascular, Inc.

[21] Appl. No.: 09/186,997

[22] Filed: Nov. 6, 1998

[51] Int. Cl.[7] .................................................. G01N 33/48

[52] U.S. Cl. ............................ 356/39; 600/322; 356/41

[58] Field of Search ............................. 356/39, 41, 40; 600/322, 323

[56] References Cited

U.S. PATENT DOCUMENTS

| | | |
|---|---|---|
| 3,922,088 | 11/1975 | Lübbers et al. . |
| 4,114,604 | 9/1978 | Shaw et al. . |
| 4,167,331 | 9/1979 | Nielsen . |
| 4,209,300 | 6/1980 | Thibault . |
| 4,227,814 | 10/1980 | Soodak et al. . |
| 4,243,883 | 1/1981 | Schwarzmann . |
| 4,303,336 | 12/1981 | Cullis . |
| 4,407,290 | 10/1983 | Wilber . |

(List continued on next page.)

OTHER PUBLICATIONS

Bellaigho et al., Venous Saturation Monitoring: Reliability of the Oxysat With and Without Use of Cuvette, 16th Annual Meeting of the Scandinavian Society for Extracorporeal Technology, p.55.

Hancock et al., “Slow Phase of Transvascular Fluid Flux Reviewed”, *Journal of Applied Physiology*, vol. 69, No. 2, pp. 456–464, Aug. 1990.

Oppenheimer et al., “Colorimetric Device for Measurement of Transvascular Fluid Flux in Blood–Perfused Organs”, *Journal of Applied Physiology*, pp. 364–372.

Reynolds et al., “Diffuse Reflectance from a Finite Blood Medium: Applications to the Modeling of Fiber Optic Catheters”, *Applied Optics*, vol. 15, No. 9, pp. 2059–2067, Sep. 1976.

Schmitt et al., An Integrated Circuit–Based Optical Sensor for in Vivo Measurement of Blood Oxygenation, *IEEE Transactions of Biomedical Engineering*, vol. BME–33, No. 2, pp. 98–107, Feb. 1986.

Schmitt et al., “New Methods for Whole Blood Oximetry”, *Annals of Biomedical Engineering*, vol. 14, pp. 35–52, 1986.

Takatani et al., “A Miniature Hybrid Reflection Type Optical Sensor for Measurement of Hemoglobin Content and Oxygen Saturation of Whole Blood”, *IEEE Transactions on Biomedical Engineering*, vol. 35, No. 3, pp. 187–198, Mar. 1988.

Vurek et al., “Oxygen Saturation Monitor for Extra–Corporeal Circulation Applications”, *Medical Instrumentation*, vol. 7, No. 4, pp. 262–267, Sep.–Oct. 973.

*Primary Examiner*—Frank G. Font
*Assistant Examiner*—Layla Lauchman
*Attorney, Agent, or Firm*—Harold R. Patton; Michael J. Jaro

[57] ABSTRACT

The present invention relates to an apparatus for monitoring blood parameters during cardio-pulmonary bypass surgery or during other procedures which utilize an extracorporeal circuit. The apparatus is typically used to monitor the percentage of hemoglobin bound with oxygen (oxygen saturation), the total amount of hemoglobin in the blood, and the percent of blood which is comprised of red blood cells (hematocrit), although the apparatus can be adapted to measure other blood parameters. The apparatus (or monitor) provides real-time results to show immediate changes (trending) in the monitored parameters.

18 Claims, 6 Drawing Sheets

U.S. PATENT DOCUMENTS 4,444,498 4/1984 Heinemann .
4,447,150 5/1984 Heinemann .
4,502,786 3/1985 Golias et al. .
4,523,279 6/1985 Sperinde et al. .
4,596,035 6/1986 Gershman et al. .
4,621,643 11/1986 New, Jr. et al. .
4,623,248 11/1986 Sperinde et al. .
4,651,741 3/1987 Passafaro .
4,694,833 9/1987 Hamaguri .
4,745,279 5/1988 Karkar et al. .
4,759,369 7/1988 Taylor .
4,776,340 10/1988 Moran et al. .
4,796,633 1/1989 Zwirkoski .
4,796,636 1/1989 Branstetter et al. .
4,797,655 1/1989 Orndah et al. .
4,800,885 1/1989 Johnson .
4,805,623 2/1989 Jöbsis .
4,810,090 3/1989 Boucher et al. .
4,846,183 7/1989 Martin .
4,854,699 8/1989 Edgar, Jr. .
4,863,265 9/1989 Flower et al. .
4,869,253 9/1989 Craig, Jr. et al. .
4,869,254 9/1989 Stone et al. .
4,925,299 5/1990 Meisberger et al. .
4,936,679 6/1990 Mersch .
4,942,877 7/1990 Sakai et al. .
4,981,355 1/1991 Higgins .
4,997,769 3/1991 Lundsgaard .
5,048,524 9/1991 Bailey ..................................... 128/634
5,058,587 10/1991 Kohno et al. .
5,061,632 10/1991 Shepherd et al. .
5,066,859 11/1991 Karkar et al. .
5,099,123 3/1992 Harjunmaa .
5,115,133 5/1992 Knudson .
5,149,503 9/1992 Kohno et al. .
5,179,951 1/1993 Knudson .
5,188,108 2/1993 Secker .
5,277,181 1/1994 Mendelson et al. .
5,280,786 1/1994 Wlodarczyk et al. .
5,285,783 2/1994 Secker .
5,285,784 2/1994 Secker .
5,288,646 2/1994 Lundsgaard et al. .
5,297,548 3/1994 Pologe .
5,318,022 6/1994 Taboada et al. .
5,331,958 7/1994 Oppenheimer .
5,341,804 8/1994 Fogt et al. .
5,351,686 10/1994 Steuer et al. .
5,356,593 10/1994 Heiberger et al. .
5,357,954 10/1994 Shigezawa et al. .
5,361,758 11/1994 Hall et al. .
5,366,903 11/1994 Lundsgaard et al. .
5,372,136 12/1994 Steuer et al. .
5,385,143 1/1995 Aoyagi .
5,385,539 1/1995 Maynard .
5,503,148 4/1996 Pologe et al. .
5,564,417 10/1996 Chance .
5,601,080 2/1997 Oppenheimer .
5,625,459 4/1997 Driver .
5,632,272 5/1997 Diab et al. .
5,673,694 10/1997 Rivers .
5,692,505 12/1997 Fouts .
5,730,125 3/1998 Prutchi et al. .
5,734,464 3/1998 Gibbs .
5,773,301 6/1998 Ziegler .
5,774,213 6/1998 Trebino et al. .
5,791,345 8/1998 Ishihara et al. ......................... 128/637

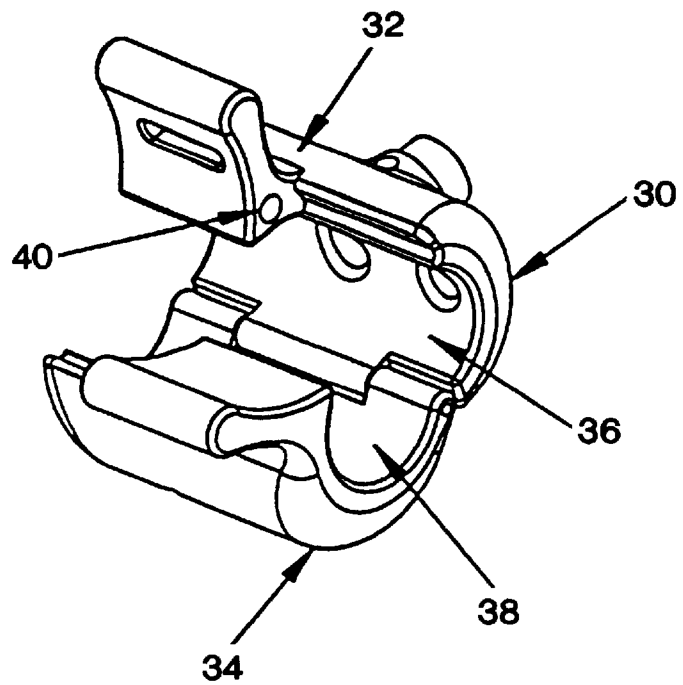
FIG. 2A
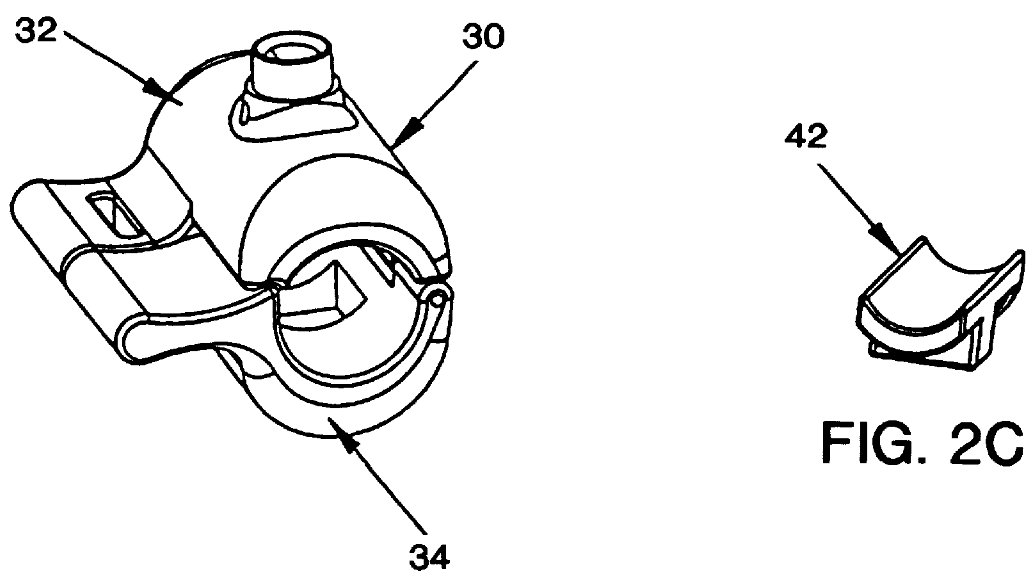
FIG. 2B
FIG. 2C

APPARATUS AND METHOD TO DETERMINE BLOOD PARAMETERS

FIELD OF THE INVENTION

This invention relates to an apparatus and method for determining parameters of blood circulating through an extracorporeal circuit. Most preferably the apparatus determines oxygen saturation, hemoglobin concentration and hematocrit.

BACKGROUND OF THE INVENTION

Oxyhemoglobin and deoxyhemoglobin differentially absorb red and infrared light. An optical oximeter uses the difference in absorption to measure blood oxygen saturation. The difference in absorption can also be used to measure hematocrit, hemoglobin and other parameters of the blood. One method for measuring hematocrit, hemoglobin and oxygen saturation is by passing red light and infrared light through blood in shorter and longer paths and using the differences in light energy remaining to calculate the desired parameters.

For some medical procedures, an extracorporeal circuit with a pump and an oxygenator is used to temporarily replace the function of the heart and lungs, respectively. To maintain proper physiological conditions, the blood's oxygen saturation and hemoglobin concentration are periodically measured by taking blood samples from the circuit and sending the samples to a clinical laboratory. In the above system, the blood parameters are not continuously monitored. This results in delay for treatment of physiological changes that may be identified by measuring oxygen saturation, hemoglobin and hematocrit.

The delay encountered when blood parameters are measured in a clinical laboratory may be eliminated by directly measuring the parameters of blood as it passes through the extracorporeal circuit. Devices which directly measure the parameters irradiate the blood and measure the reflected or transmitted light to calculate the blood parameters. However, these devices unnecessarily add to the complexity of the circuit requiring that additional devices, such as cuvettes, be plumbed into the circuit's conduit. Further, because an apparatus must be plumbed into the circuit, the measurements are taken at a fixed location within the extracorporeal circuit. The operator has no ability to monitor blood parameters at other locations. Also, the splicing of elements into the circuit provides a point for the introduction of pathogens and other contaminants through improper sterilization or during the process of inserting the apparatus into the circuit.

Other types of detectors suffer from further disadvantages. Some detectors require sensors to physically contact the blood in order to measure the intensity of reflected light. These devices suffer from inaccuracy due to changes over time in the detector under the influence of the blood's physical properties. This alters the measurement of the reflected light detected resulting in an inaccurate measurement of the blood's characteristics. Further, there is a risk of electrical leakage from the electric components that could be detrimental to the patient.

The present invention provides an apparatus and method for measuring blood parameters by attaching sensors to the conduit of an extracorporeal circuit. Thus, the present invention provides numerous advantages over prior art devices. For example, the present invention eliminates the need for placing sensors in direct contact with the blood and the need for plumbing additional elements into the extracorporeal circuit. Further, the present invention provides the operator with the flexibility to move the clamp to different locations on the extracorporeal circuit's conduit during an operation (e.g. from the venous to the arterial side of the circuit). Also, since the device does not contact the blood, the clamp does not need to be sterilized and there is no risk of electrical leakage.

SUMMARY OF THE INVENTION

In one aspect, this invention is an apparatus for monitoring blood parameters during cardio-pulmonary bypass surgery or during other procedures which utilize an extracorporeal circuit. The apparatus is typically used to monitor the percentage of hemoglobin bound with oxygen (oxygen saturation), the total amount of hemoglobin in the blood, and the percent of blood which is comprised of red blood cells (hematocrit), although the apparatus can be adapted to measure other blood parameters. The apparatus (or monitor) provides real-time results to show immediate changes (trending) in the monitored parameters.

In one aspect, the apparatus has a light source which transmits light at a plurality of wavelengths to the conduit. Some of the light source's light is transmitted and some is absorbed by the blood. The reflected or transmitted light is received by a near sensor and a far sensor. The near sensor is connected to receive light a first distance from the light source. The near sensor senses the intensity of light at a plurality of wavelengths. The near sensor generates a signal indicative of the intensity of the sensed light at a plurality of wavelengths. The far sensor is also connected to receive light but at a second distance from the light source not equivalent to that of the first distance. The far sensor also senses the intensity light at a plurality of wavelengths. The far sensor generates a signal indicative of the intensity of light at a plurality of wavelengths. An arithmetic circuit receives the signals from the near sensor and the far sensor and calculates at least one parameter of blood, therefrom. The arithmetic circuit then generates an output signal indicative of the signals.

The light source emits wavelengths between 450 nm and 1150 nm. The light source can be a tungsten halogen bulb or any other bulb, set of bulbs or set of diodes emitting a sufficient intensity of light at the desired wavelengths.

The near sensor is preferably a first charge coupled device and the far sensor is preferably a second charge coupled device of a single two-channel spectrometer. Alternatively, the near sensor could be a first spectrometer and the far sensor could be a second spectrometer.

The arithmetic circuit could derive the blood oxygen saturation from the ratios of reflected light at wavelengths between 660 nm and 815 nm in accordance with the formula: $\text{oxygen saturation}=A(n680nm/n815nm)^3+B(n680nm/n815nm)^2+C(n680nm/n815nm)+D(n680nm/n815nm)^{-1}+E(n680nm/n815nm)^{-2}+F(n710nm/n740nm)^3+G(n710nm/n740nm)^2+H(n710nm/n740nm)+I(n710nm/n740nm)^{-1}+J(n710nm/n740nm)^{-2}+L(n760nm/n815nm)^3+M(n760nm/n815nm)^2+N(n760nm/n815nm)+O(n760nm/n815nm)^{-1}+P(n760nm/n815nm)^{-2}+T(f680nm/f815nm)^3+U(f680nm/f815nm)^2+V(f680nm/f815nm)+W(f680nm/f815nm)^{-1}+X(f680nm/f815nm)^{-2}+Y(f710nm/f740nm)^3+Z(f710nm/f740nm)^2+AA(f710nm/f740nm)+BB(f710nm/f740nm)^{-1}+CC(f710nm/f740nm)^{-2}+DD(f760nm/f815nm)^3+EE(f760nm/f815nm)^2+FF(f760nm/f815nm)+GG(f760nm/f815nm)^{-1}+HH(f760nm/f815nm)^{-2}+II(n815nm/f810nm)^3+JJ(n815nm/f810nm)^2+KK(n815nm/f810nm)+LL$ wherein A to LL are constants, n designates the reflectance detected by the near sensor, and f designates the reflectance detected by the far sensor. Although, any formula from which blood oxygen saturation is derived using a plurality of wavelengths measured at near and far sensors would be sufficient.

The arithmetic circuit could derive one of hemoglobin concentration and hematocrit from the ratios of reflected light at a plurality of wavelengths between 760 nm and 999 nm in accordance with the formula: hemoglobin and hematocrit=$A(n815nm/f810nm)^3+B(n815nm/f810nm)^2+C(n815nm/f810nm)+D(n815nm/f810nm)^{-1}+E(n815nm/f810nm)^{-2}+F(n850nm/f825nm)^3+G(n850nm/n825nm)^2+H(n850nm/f825nm)+I(n850nm/f825nm)^{-1}+J(n850nm/f825nm)^{-2}+O(n880nm/f827nm)^3+P(n880nm/f827nm)^2+Q(n880n/f827nm)+R(n880nm/f827nm)^{-1}+S(n880nm/f827nm)^{-2}+U(n900nm/f830nm)^3+V(n900nm/f830nm)^2+W(n900nm/f830nm)+X(n900nm/f830nm)^{-1}+Y(n900nm/F830nm)^{-2}+Z(n999nm/f935nm)^3+AA(n999nm/f935nm)^2+BB(n999nm/f935nm)+CC(n999nm/f935nm)^{-1}+DD(n999nm/f935nm)^{-2}+EE(n760nm/n815nm)^3+FF(n760nm/n815nm)^2+GG(n760nm/n815nm)+HH$ when blood hemoglobin concentration is less than 9 or hematocrit is less than 25; and hemoglobin and hematocrit=$A(n802nm^{N1}/f802nm^{D1})^3+B(n802nm^{N1}/f802nm^{D1})^2+C(n802nm^{N1}/f802nm^{D1})+D(n802nm^{N1}/f802nm^{D1})^{-1}+E(n802nm^{N1}/f802nm^{D1})^{-2}+I(n803nm^{N2}/f803nm^{D2})^3+J(n803nm^{N2}f803nm^{D2})^2+K(n803nm^{N2}/f803nm^{D2})+L(n803nm^{N2}/f803nm^{D2})^{-1}+M(n803nm^{N2}/f803nm^{D2})^{-2}+O(n805nm^{N3}/f802nm^{D2})^3+P(n805nm^{N3}/f802nm^{D3})^2+Q(n805nm^{N3}/f802nm^{D3})+R(n805nm^{N3}/f802nm^{D3})^{-1}+S(n805nm^{N3}/f802nm^{D3})^{-2}+U(n810nm^{N4}/f803nm^{D4})^3+V(n810nm^{N4}/f803nm^{D4})^2+W(n810nm^{N4}/f803nm^{D4})+X(n810nm^{N4}/f803nm^{D4})^{-1}+Y(n810nm^{N4}/f803nm^{D4})^{-2}+FF(n760nm/n815nm)^3+GG(n760nm/n815nm)^2+HH(n760nm/n815nm)+II$ when blood hemoglobin concentration is greater than or equal to 9 or hematocrit is greater than or equal to 25 wherein, A to LL are constants, n designates the reflectance detected by the near sensor, and f designates the reflectance detected by the far sensor. Although, any formula from which hemoglobin and/or hematocrit are derived using a plurality of wavelengths measured at near and far sensors would be sufficient.

The apparatus preferably uses a source optical fiber to transmit light from the light source to the conduit. The source optical fiber having a first end connected to the light source and a second terminal end connected adjacent the conduit. Preferably, the near sensor receives light from a near optical fiber. The near optical fiber having a first end connected to the near sensor and a second terminal end connected adjacent the conduit. Preferably, the far sensor receives light from a far optical fiber. The far optical fiber having a first end connected to the far sensor and a second terminal end connected adjacent the conduit.

The apparatus preferably includes a clamp. The clamp secures a terminal end of the source optical fiber, a terminal end of the near optical fiber and a terminal end of the far optical fiber such that the source fiber, the near optical fiber and the far optical fiber are in optical communication with the extracorporeal circuit's conduit. The clamp preferably secures the terminal ends of the source optical fiber, the near optical fiber and the far optical fiber such that the terminal ends of the optical fibers are biased against the conduit. The clamp preferably secures the terminal ends such that the ends are oriented substantially perpendicular to the fluid flow through the conduit.

The terminal ends of the near and far optical fibers are differentially spaced from the terminal end of the source optical fiber. The terminal end of the near optical fiber is preferably positioned about 0.8 mm from the terminal end of the source optical fiber. The terminal end of the far optical fiber is preferably positioned about 1.2 mm from the terminal end of source optical fiber. The terminal ends of the near optical fiber, the far optical fiber and the source optical fiber can positioned co-axially along the flow path of blood in the conduit.

In another aspect, the invention is a method for measuring a blood parameter. The method includes passing through a conduit in an extracorporeal circuit with a blood monitor having a light source, a near sensor and a far sensor. The light source emits a plurality of wavelengths through the conduit into the blood. The light reflected by the blood is directed to the near sensor. The light reflected by the blood is also directed to the far sensor. The quantity of reflected light received by the blood at the near sensor and the far sensor is measured at a plurality of wavelengths. The measured quantity of reflected light at the near sensor and the far sensor is used to calculate the desired blood parameter using a plurality of wavelengths.

In another aspect, the invention is a method for measuring a blood parameter using a clamp to mount optical fibers to the conduit. The method includes providing a blood monitor having a near sensor, a far sensor and a light source which are connected by optical fibers to a clamp. The clamp is mounted on the conduit in a manner such that terminal ends of the optical fibers are held against the outer surface of the conduit. Light is emitted at a plurality of wavelengths through the conduit into the blood. The light reflected by the blood at a plurality of wavelengths is received by the sensors. The light received by the near and the far sensors is quantitated at a plurality of wavelengths. The values for blood parameters are then calculated from the quantity of reflected light.

In another aspect, the invention is a clamp for positioning optical fibers against a conduit to measure reflected light. The clamp includes a body defining a cavity shaped to accept the conduit and a mating piece movably attached to the body. The mating piece is shaped so as to cooperate with the body to securedly hold the conduit. The mating piece is preferably hingedly attached to the body. At least two optical fibers mounted in the body, wherein terminal ends of the optical fibers extend into the cavity. The body and mating piece cooperate to hold the conduit such that in a closed position the conduit is compressionally biased against the terminal ends of the optical fibers. The clamp can include a lock for maintaining the mating piece in the closed position. The clamp can have the terminal ends of the optical fibers positioned co-axially along the flow path of blood in the conduit. The clamp can secure three optical fibers, a first fiber, a second fiber secured about 0.8 mm from the first fiber and a third fiber secured about 1.2 mm from the light source.

In another aspect, the invention is a clamp for positioning optical fibers against a conduit for measuring blood parameters using transmitted light. The clamp includes a body defining a cavity shaped to accept conduit At least one optical fiber is secured in the body with the terminal end of the optical fiber extending into the cavity. A mating piece movably attached to the body. The cavity and the mating piece shaped so as to cooperate in securing the conduit when in a closed position. At least two optical fibers are mounted in the mating piece such that terminal ends of the fibers extend into the are positioned opposite the cavity so as to receive light transmitted through the blood from an optical fiber in the cavity of the body. The terminal ends of the optical fibers are positioned such that they are compressionally biased against the conduit when the conduit is held in the clamp.

In another aspect, the invention is a method for calibrating a blood monitor. The monitor to be calibrated having a light source and a spectrometer with at least one charge coupled device array which measures blood parameters in an extracorporeal circuit. The method including masking pixels of the charge coupled device array. A dark reference is measured from the masked pixels of the charge coupled device array. A light reference is measured using the light from the light source reflected by a diffuse reflective material. The values for reflected light are normalized using the measured light reference and the measured dark reference.

In another aspect, the invention is a method of regulating use of a medical monitor. The method for regulating uses includes providing a key encoded with data indicative of a pre-selected number of uses and providing firmware in the monitor which recognizes the data encoded key. The firmware and the data encoded key are electrically connected wherein the data encoded key activates the monitor for the pre-selected number of uses. A use can include continuously running of the monitor for eight hours, removing of the clamp for a specified period of time or any other activity indicative of a complete cycle of use.

Alternatively, the method of regulating use of the medical monitor includes providing circuitry to disable the monitor and providing firmware in the monitor that can be programmed for a pre-selected number of uses. The firmware is coupled to the disabling circuitry in a manner so as to disable the monitor after the pre-selected number of uses.

BRIEF DESCRIPTION OF THE DRAWINGS

FIG. 2*a* is a perspective view of an embodiment of the clamp in the open position;

FIG. 2*b* is a perspective view of an embodiment of the clamp in the closed position;

FIG. 2*c* is a perspective view of an embodiment of the adapter insert;

DETAILED DESCRIPTION OF THE INVENTION

The present invention is a monitor or apparatus for monitoring blood parameters and utilizes a polychromatic light beam which is directed into blood. The extent of absorption, refraction, scattering and reflection of the light is determined by the chemistry and physical properties of the blood. Incident light is absorbed, refracted, scattered and reflected by the blood. At each wavelength, a fraction of incident light is either absorbed, scattered or reflected. This absorbed, scattered or reflected light can be detected by sensors in order to measure and monitor oxygen saturation, hematocrit, hemoglobin, oxyhemoglobin, deoxyhemoglobin, carboxy-hemoglobin, methoxy-hemoglobin, and bilirubin and further can determine cell counts for erythrocytes and platelets.

Figure 1:
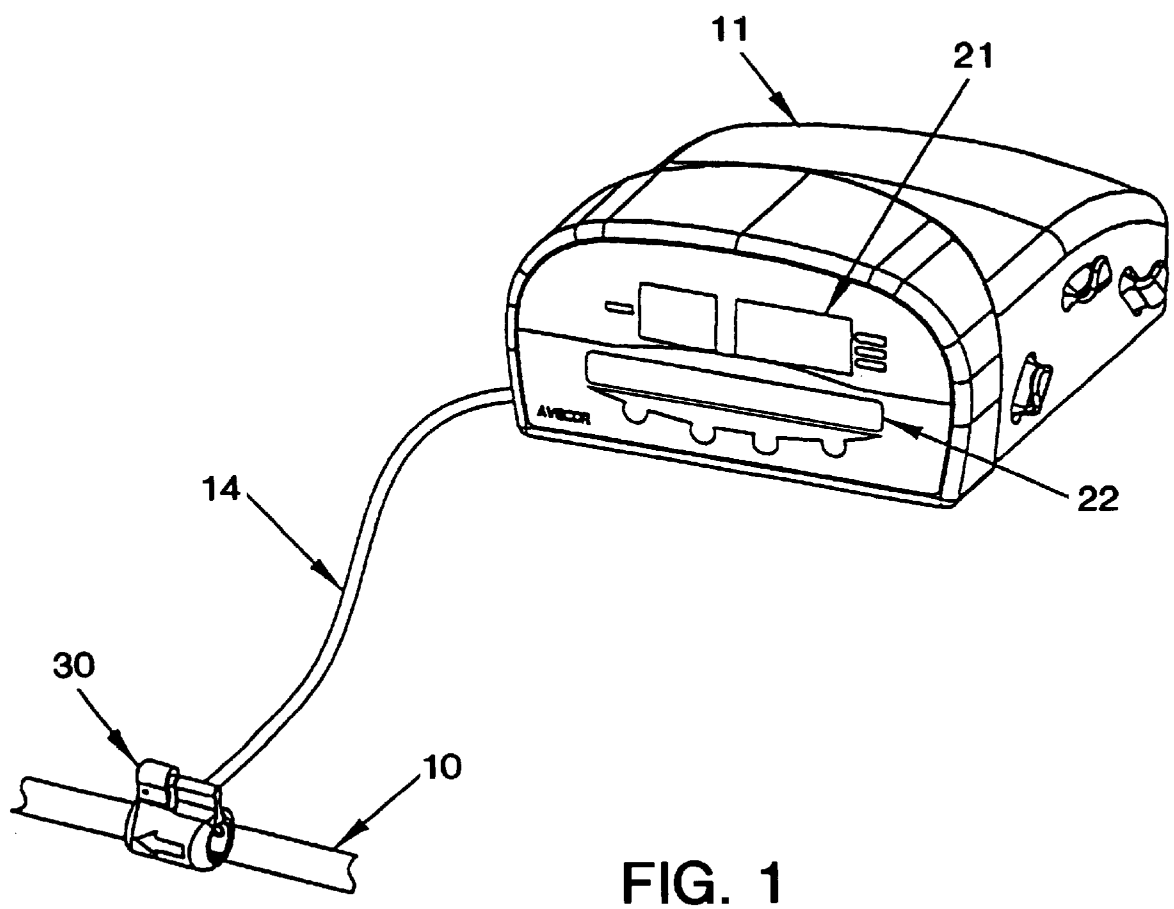
FIG. 1 is a view of a preferred embodiment of the blood monitor.

The diagram of FIG. 1 shows an embodiment of the instant invention used for measuring blood parameters, in particular for measuring oxygen saturation, hematocrit and hemoglobin. The diagram shows clamp 30 secured to conduit 10 of an extracorporeal circuit. Clamp 30 securely holds the ends of optical fibers contained in fiber optic cable 14. Conduit 10 can be any optically clear element of the extracorporeal circuit through which blood within the circuit passes, such as a cuvette, but is preferably optically clear tubing or more preferably clear polyvinylchloride (PVC) tubing. An optical fiber directs light to the blood from a light source located in housing 11. A plurality of optical fibers receive light reflected from the blood and direct light to one or more spectrometers located in housing 11. Clamp 30 secures the ends of the optical fibers to the conduit 10 such that the blood flows through conduit 10 substantially perpendicular to the optical fibers. In a preferred embodiment, the housing includes a numeric display 21 displaying the values for oxygen saturation, hematocrit and hemoglobin concentration. In a more preferred embodiment, numeric display 21 is a monitor having five seven-segment LED's displaying the parameters. The housing can also contain an alphanumeric display 22 to communicate information to the perfusionist regarding the status of the monitor and the patient. In a preferred embodiment, alphanumeric display 22 is a vacuum fluorescent display (VFD). Further, housing 18 preferably includes the controls for the operation and adjustment of the monitor and selection of the blood parameter to be displayed.

FIGS. 2*a*, 2*b* and 2*c* show a preferred embodiment of conduit clamp 30. Conduit clamp 30 is composed of a body 32 and a mating piece 34. Body 32 defines a cavity 36 shaped to secure conduit 10 of an extracorporeal circuit. Mating piece 34 defines a cavity 38 and is attachable to body 32 such that the mating piece 34 can be in an open position, shown in FIG. 2*a*, or a closed position, shown in FIG. 2*b*. In a preferred embodiment mating piece 34 is hingedly attached to body 32 and is provided with a locking apparatus 40 to secure body 32 and mating piece 34 in the closed position. Most preferably, locking apparatus 40 is a stainless steel short spring plunger and detent so clamp 30 is not accidentally removed from conduit 10. When in the closed position body cavity 36 and mating piece cavity 38 cooperate to secure conduit 10.

In an alternative embodiment cavity 38 is provided with an adapter 42 allowing smaller diameter or alternatively shaped conduit to be secured in clamp 30. The design of clamp 30 provides increased ambient light isolation and easy placement anywhere on the extracorporeal circuit. For example, the operator can place the clamp on conduit either upstream or downstream of the oxygenator allowing measurement of the parameters of venous or arterial blood, respectively.

In another alternative embodiment, not shown, a near optical fiber and a far optical fiber are mounted on a mating piece on the opposite side of conduit 10 from the light source such that the optical fibers are differentially spaced from the light source and detect light transmitted through the blood flowing through the conduit as opposed to reflected light. Most preferably, the mating piece is configured such that, in the closed position, the ends of the optical fibers are biased against the conduit of the circuit. In order for the sensors to be able to pick up sufficient transmitted light so that the desired parameters can be measured, the conduit should be of a diameter small enough such that sufficient light from the light source is transmitted through the blood and received by the near and far sensors that are differentially spaced from the light source. Additionally or alternatively, the light source's intensity could be increased such that light from light source is capable of penetrating the blood flowing through standard sized extracorporeal circuit conduit to reach the sensors mounted on the mating piece opposite the light source.

Figure 3A:
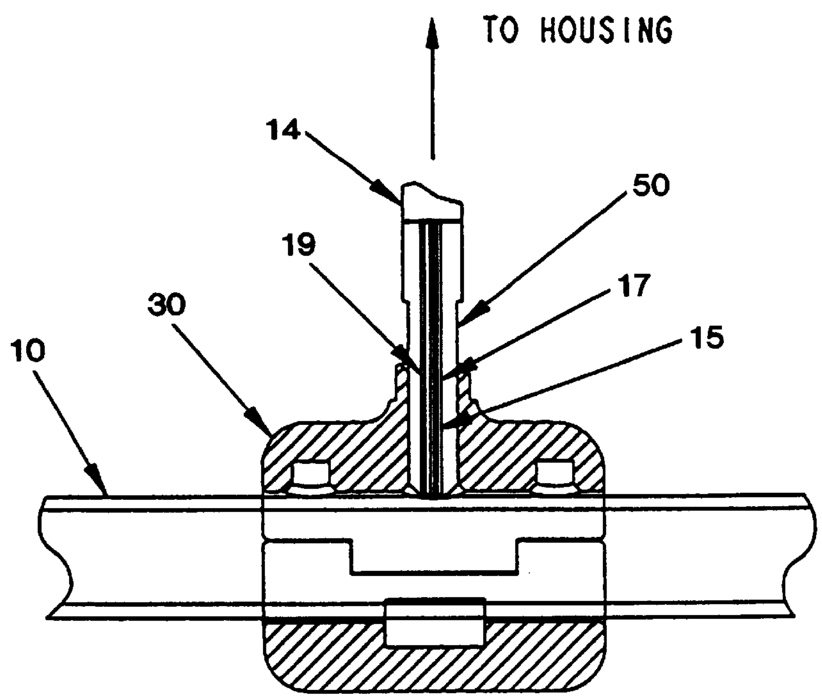
FIG. 3*a* is an enlarged cross-sectional view from the top of an embodiment of the clamp.
Figure 3B:
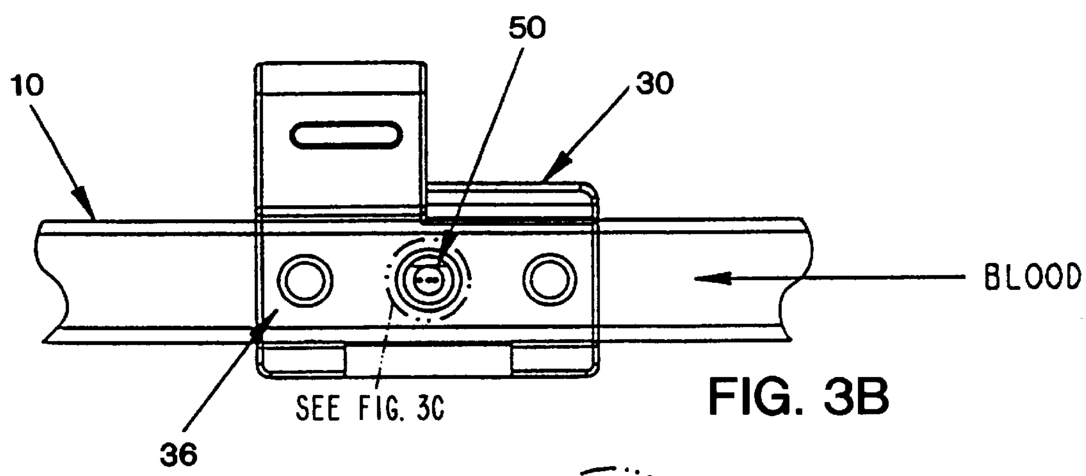
FIG. 3*b* is an enlarged cross-sectional view from the front of an embodiment of the clamp.
Figure 3C:
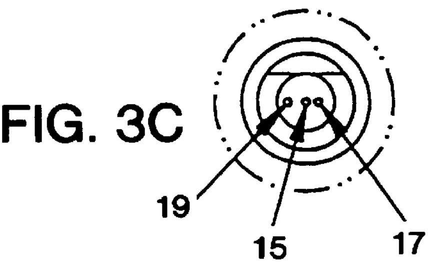
FIG. 3*c* is a detailed view of the terminal ends of the optical fibers.

FIGS. 3*a*, 3*b* and 3*c* show detailed cross sectional views of an embodiment of clamp 30. In this embodiment, a ferrule 50 securedly holds the terminal ends of three optical fibers. An optical fiber 15 is in optical communication with the light source 16. A near optical fiber 17 is in optical communication with near sensor 18. A far optical fiber 19 is in optical communication with far sensor 20. Preferably, the ends of the optical fibers are positioned substantially coplanar with the end of ferrule 50. Further, the ends of the optical fibers are preferably polished such that light transmitted or received is not distorted by irregularities in the ends of the optical fibers. Ferrule 50 is securedly mounted in body 32 such that optical fiber 15, near optical fiber 17 and far optical fiber 19 are in optical communication with conduit 10. Clamp 30 positions ferrule 50 relative to conduit 10 such that light transmitted from light source 16 passes through optical fiber 15 and conduit 10. The path of light emitted from optical fiber 15 is preferably substantially perpendicular to the flow of blood within conduit 10. The light reflected by the blood passes back through conduit 10 and is transmitted by near optical fiber 17 and far optical fiber 19 to near sensor 18 and far sensor 20, respectively. In a more preferred embodiment, the end of ferrule 50 extends through body 32 beyond the inner wall of cavity 36 such that conduit 10 held by clamp 30 is biased against the end of the ferrule 50 as shown in FIG. 3*a*. This biased configuration assures that there is no space between conduit 10 and ferrule 50 and therefore, no disruption of the light path. In an alternative embodiment, not shown, ferrule 50 and body 32 are integrated into a single element securing optical fiber 15, near optical fiber 17 and far optical fiber 19.

Near optical fiber 17 and far optical fiber 19 receive light at different distances from optical fiber 15. The near and far optical fibers are positioned from between about 0.6 mm to about 3.0 mm from optical fiber 15 such that a sufficient amount of light is received by far optical fiber 19 to produce the data necessary to calculate the desired parameters. In a preferred embodiment, near optical fiber 17 receives light at a distance of about 0.8 mm from optical fiber 15 and far optical fiber 19 receives light at a distance of about 1.2 mm from optical fiber 15. In a most preferred embodiment, the optical fibers are positioned axially along the blood's flow path wherein, near optical fiber 17 is located 0.8 mm upstream from optical fiber 15 and far optical fiber 19 is located 1.2 mm downstream from optical fiber 15.

Figure 4:
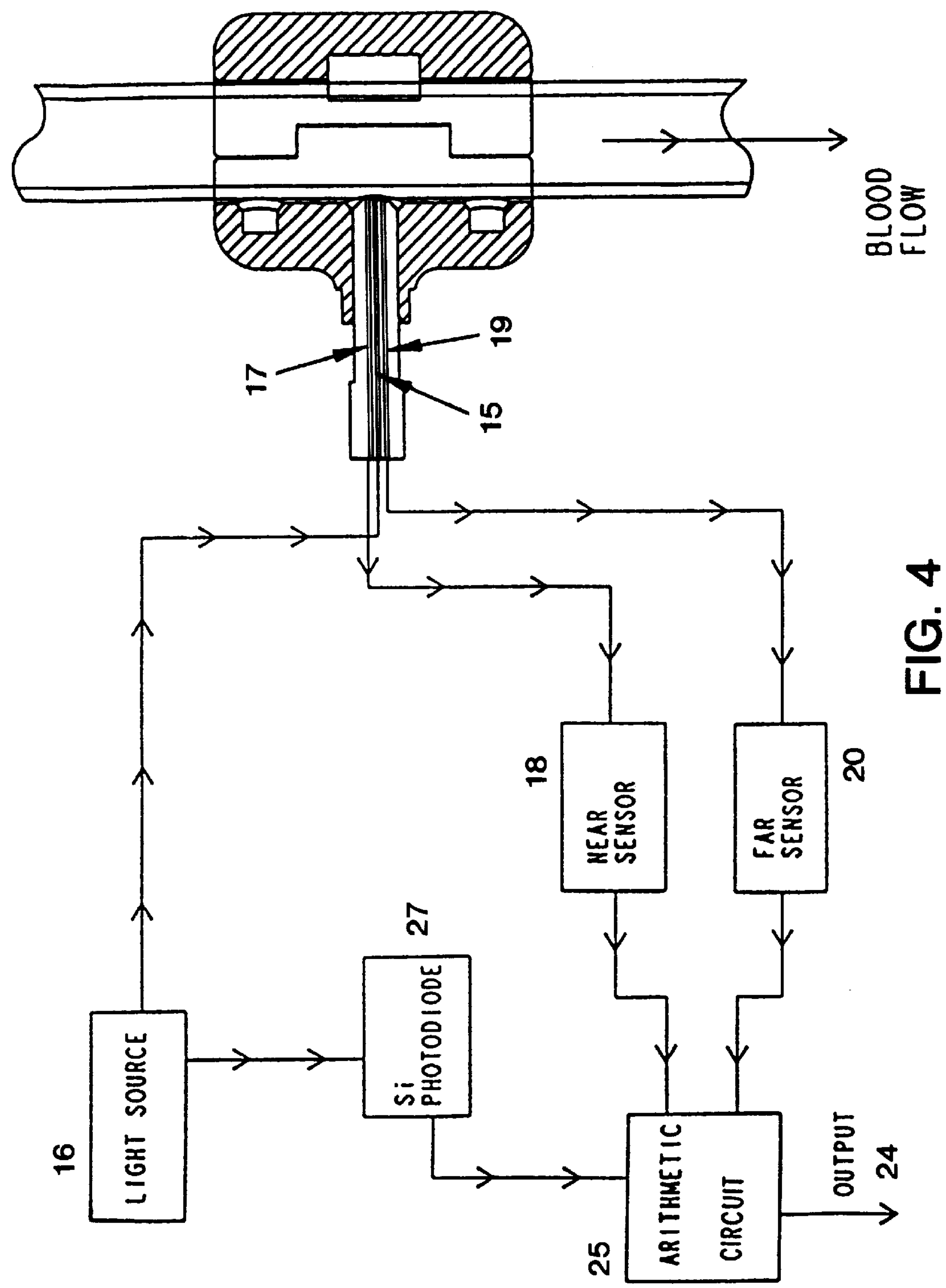
FIG. 4 is a block diagram of an embodiment of the blood monitor's operation.

The block diagram of FIG. 4 shows the mechanism of the monitor's operation. Light source 16 directs light into blood flowing through conduit 10. The light is absorbed, refracted, scattered and reflected by the blood. Reflected light is received by near optical fiber 17 and far optical fiber 19 and is transmitted to near sensor 18 and far sensor 20, respectively. The near and far sensors quantitate the light received at a plurality of wavelengths. The light's intensity is normalized at each of the plurality of wavelengths by the arithmetic circuit 25. The arithmetic circuit 25 then uses the normalized intensities to calculate the values for the blood parameters and produce an output 24. In another embodiment, an additional optical fiber guides light from the light source to a silicone photodiode 27. Photodiode 27 provides an extra measure of safety in case of burnout of the light source as well as providing trending of light source's intensity.

In one embodiment, light source 16 directs a plurality of wavelengths between about 300 nm to about 10,000 nm and more preferably between about 405 nm and about 1100 nm into conduit 10. Most preferably, the light source 16 is a tungsten halogen bulb, although any bulb emitting a sufficient intensity of light over the desired spectrum could be used. In another embodiment, a plurality of light sources each emitting discrete spectra, such as light emitting diodes (LEDs), are used to emit the desired wavelengths of light. The plurality of light sources are either combined or sequentially emitted and directed to a single point along the extracorporeal circuit using optical fiber 15.

In a preferred embodiment, near sensor 18 is a first channel of a two-channel spectrometer receiving light from near optical fiber 17 and far sensor 20 is a second channel of the spectrometer receiving light from far optical fiber 19. The first and second channels are separate optical blocks electronically connected as a single two-channel spectrometer. Alternatively, near sensor 18 could comprise a first spectrometer receiving light from near optical fiber 17 and the far sensor could comprise a second spectrometer receiving light from far optical fiber 19. In still another embodiment, the near and far sensors could share a single spectrometer having a single channel switching between and separately quantitating light received from near optical fiber 17 and far optical fiber 19. Regardless of configuration, the sensors quantitate the amount of light received from near optical fiber 17 and far optical fiber 19 at a plurality of wavelengths and transmit the data to the arithmetic circuit 25. The arithmetic circuit 25 then calculates the values for oxygen saturation, hematocrit and hemoglobin concentration using the input from near sensor 18 and far sensor 20.

Before using the monitor, a two-point calibration is performed. The two-point calibration establishes a light reference and a dark reference. The dark reference measures the electrical stability of the optical system. The dark reference is determined by measuring the output from masked pixels of the spectrometer's CCD (charge coupled device) array. The light reference measures the intensity of the light source. The light reference is the intensity of reflected light received by the near and far optical fibers from a diffuse reflective material. The light reference is taken without tubing or other obstruction in the light path. The values for the light reference and a first dark reference are recorded and stored for data normalization.

Figure 5:
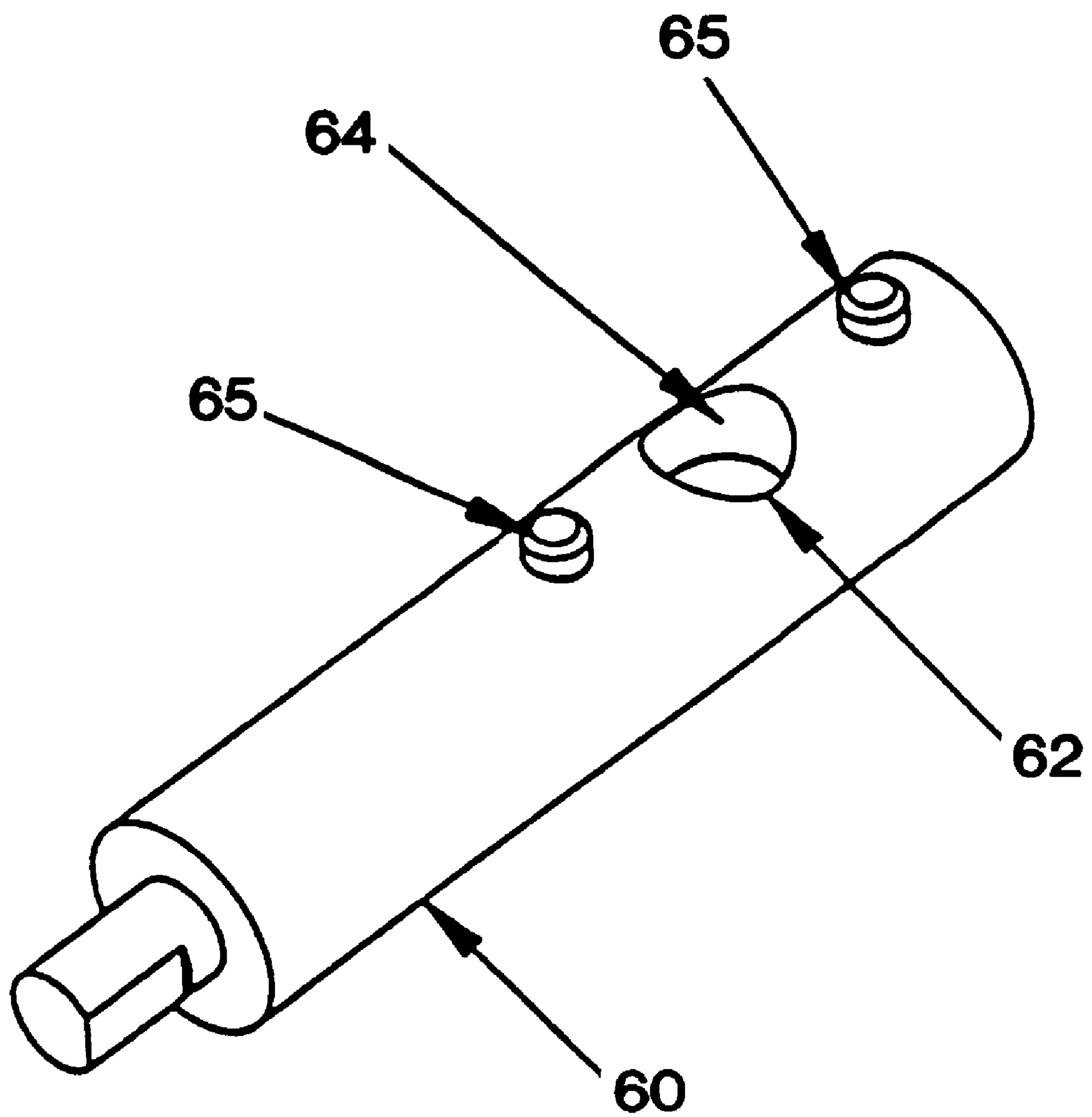
FIG. 5 is a perspective view of an embodiment of the calibration post.

To perform a two-point calibration, clamp 30 is preferably mounted on a calibration post 60, shown in FIG. 5. Post 60 is shaped such that the post can be securedly held by clamp 30. Post 60 defines a cavity 64 in which diffuse reflective material 62 is located. The cavity provides an unobstructed path for light emitted from source fiber 15 and reflected from diffuse reflective material 62 to be received by near optical fiber 17 and far optical fiber 19. Diffuse reflective material 62 is preferably a sputtered gold mirror or a material with similar reflective properties such as that commercially available as Spectralon® from Labsphere®, Inc. located in North Sutton, N.H. In a preferred embodiment, one or more alignment pins 65 are provided on calibration post 60 such that the alignment pins cooperate with cavities on clamp 30 to secure diffuse reflective material 62 in the proper orientation for calibration. When clamp 30 is mounted on post 60, optical fiber 15 is oriented above the cavity such that light is emitted in a direction substantially perpendicular to the plane of the reflective material 62. In an alternative embodiment, mating piece cavity 38 is positioned opposite ferrule 50 and contains a calibrated diffuse reflective material for measuring the light reference. In a most preferred embodiment, during a two-point calibration, the monitor senses when either the angle of incidence or the intensity of the light reference are incorrect and displays an error message on the alphanumeric display.

In operation, light source 16 is turned on and clamp 30 is placed on post 60. After emissions from light source 16 have stabilized the monitor measures light received by near optical fiber 17 and far optical fiber 19 and stores the measurement as the light reference for near sensor 16 and far sensor 18, respectively. The CCD array's masked pixels for both near sensor 16 and far sensor 18 are also measured and stored during calibration to establish a dark reference. After the two-point calibration is performed the clamp is placed on the conduit of the extracorporeal circuit.

The data from the two-point calibration is used to normalize data used to calculate the blood parameters. The data is normalized pursuant to the formula:

$$(I_{normalized})_{\lambda}=(I_{\lambda}-I_{dark})_{t=t}/((I_{light})_{\lambda}-I_{dark})_{t=0} \quad \text{(Equation 1)}$$

wherein, "I" is the intensity of light, t=0 is the time of calibration, t=t is the time at which intensity is measured, and λ is a wavelength at which the reflectance is measured. A first dark reference, $I_{dark}$, is obtained at t=0. The light reference, $I_{light\lambda}$, is also obtained at t=0 after stabilization of the intensity of the light source's emission spectra. The light and first dark references are used in Equation 1 to normalize the data and remain constant until another two-point calibration is initiated. In finding the normalized intensity, $I_{normalized\lambda}$, the arithmetic circuit 25 receives the input of the reflected intensity, $I_{\lambda}$, at a plurality of wavelengths. The reflected intensity is the intensity of light received by near optical fiber 17 and far optical fiber 19 at time t=t after transmission of light through the conduit, reflectance of light by the blood and transmission back through the conduit to the sensors. A second dark reference, $I_{dark}$, is also taken at time t=t by again sampling the masked pixels of the CCD array. The second dark reference measures the electrical stability of the optical system at the time t=t and may vary unlike the first dark reference. The normalized intensity, $I_{normalized\lambda}$, resulting from Equation 1 is used by the arithmetic circuit 25 to calculate the desired blood parameters.

The arithmetic circuit 25 preferably uses a third order polynomial equation to calculate the desired blood parameters. The variables input into the equation to calculate hematocrit, hemoglobin and oxygen saturation are ratios of the normalized intensities of a plurality of wavelengths in a range between 405 nm and 999 nm received by the near and far sensors. The individual third order polynomial equations used for calculating oxygen saturation, hematocrit and total hemoglobin are established using non-linear multi-variable regression analysis. The regression analysis can be accomplished using a standard statistical program, such as that commercially available as Statistica® from StatSoft®, Inc. located in Tulsa, Okla. The data for regression analysis is obtained by measuring the reflection of blood with defined parameters at the selected wavelengths with an acceptable laboratory instrument or other suitably accurate means. To assure accurate measurements a total of at least four wavelengths are input into the equation. At least one of the wavelengths used in the equation should be selected from the range of isobestic wavelengths for hemoglobin. The isobestic wavelengths for hemoglobin fall in the range between 802 nm and 815 nm. Preferably the wavelengths are selected from the group consisting of 680 nm, 710 nm, 740 nm, 760 nm, 802 nm, 803 nm, 805 nm, 810 nm, 815 nm, 825 nm, 827 nm, 830 nm, 850 nm, 880 nm, 900 nm, 935 nm, and 999 nm. The wavelengths input into the arithmetic apparatus are selected on the basis of spectral absorption curves of the blood parameters.

In a most preferred embodiment, the third order polynomial for measuring the oxygen saturation (Sat) is the formula:

Sat=A(n680nm/n815nm)$^{3}$+B(n680nm/n815nm)$^{2}$+C(n680nm/n815nm)+D(n680nm/n815nm)$^{-1}$+E(n680nm/n815nm)$^{-2}$+F(n710nm/n740nm)$^{3}$+G(n710nm/n740nm)$^{2}$+H(n710nm/n740nm)+I(n710nm/n740nm)$^{-1}$+J(n710nm/n740nm)$^{-2}$+L(n760nm/n815nm)$^{3}$+M(n760nm/n815nm)$^{2}$+N(n760nm/n815nm)+O(n760nm/n815nm)$^{-1}$+P(n760nm/n815n)$^{-2}$+T(f680nm/f815nm)$^{3}$+U(f680nm/f815nm)$^{2}$+V(f680nm/f815nm)+W(f680nm/f815nm)$^{-1}$+X(f680nm/f815nm)$^{-2}$+Y(f710nm/f740nm)$^{3}$+Z(f710nm/f740nm)$^{2}$+AA(f710nm/f740nm)+BB(f710nm/f740nm)$^{-1}$+CC(f710nm/f740nm)$^{-2}$+DD(f760nm/f815nm)$^{3}$+EE(f760nm/f815nm)$^{2}$+FF(f760nm/f815nm)+GG(f760nm/f815nm)$^{-1}$+HH(f760nm/f815nm)$^{-2}$+II(n815nm/f810nm)$^{3}$+JJ(n815nm/f810nm)$^{2}$+KK(n815nm/f810nm)+LL wherein A to LL are constants established by non-linear multi-variable regression analysis and "n" designates the normalized intensity of light received by the near sensor at the respective wavelength and "f" designates the normalized intensity of light received by the far sensor at the respective wavelength.

In a most preferred embodiment, the arithmetic means bifurcates the calculation of hemoglobin and hematocrit between two formulas dependent on the concentration of total hemoglobin (Hgb) and the hematocrit (Hct) in the sample being monitored. The arithmetic means bifurcates the calculation because the curves generated by the third order polynomial equations are non-monotonic curves over certain ranges of total hemoglobin and hematocrit. Therefore, two separate equations were developed wherein the curves are monotonic over alternative ranges. The first equation is monotonic over a low range corresponding to a Hct of less than twenty five or alternatively, a Hgb of less than nine. The second equation is monotonic over a high range corresponding to a Hct of greater than or equal to twenty five or alternatively, a Hgb of greater than or equal to nine. If the value falls into the low range the arithmetic circuit 25, most preferably, uses the formula:

Hgb or Hct=A(n815nm/f810nm)$^{3}$+B(n815nm/f810nm)$^{2}$+C(n815nm/f810nm)+D(n815nm/f810nm)$^{-1}$+E(n815nm/f810nm)$^{-2}$+F(n850nm/f825nm)$^{3}$+G(n850nm/n825nm)$^{2}$+H(n850nm/f825nm)+I(n850nm/f825nm)$^{-1}$+J(n850nm/f825nm)$^{-2}$+O(n880nm/f827nm)$^{3}$+P(n880nm/f827nm)$^{2}$+Q(n880nm/f827nm)+R(n880nm/f827nm)$^{-1}$+S(n880nm/f827nm)$^{-2}$+U(n900nm/f830nm)$^{3}$+V(n900nm/f830nm)$^{2}$+W(n900nm/f830nm)+X(n900nm/f830nm)$^{-1}$+Y(n900nm/F830nm)$^{-2}$+Z(n999nm/f935nm)$^{3}$+AA(n999nm/f935nm)$^{2}$+BB(n999nm/f935nm)+CC(n999nm/f935nm)$^{-1}$+DD(n999nm/f935nm)$^{-2}$+EE(n760nm/n815nm)$^{3}$+FF(n760nm/n815nm)$^{2}$+GG(n760nm/n815nm)+HH

If the values fall into the high range, the arithmetic circuit 25 most preferably uses the formula:

Hgb or Hct=A(n802nm$^{N1}$/f802nm$^{D1}$)$^{3}$+B(n802nm$^{N1}$/f802nm$^{D1}$)$^{2}$+C(n802nm$^{N1}$/f802nm$^{D1}$)+D(n802nm$^{N1}$/f802nm$^{D1}$)$^{-1}$+E(n802nm$^{N1}$/f802nm$^{D1}$)$^{-2}$+I(n803nm$^{N2}$/f803nm$^{D2}$)$^{3}$+J(n803nm$^{N2}$f803nm$^{D2}$)$^{2}$+K(n803nm$^{N2}$/f803nm$^{D2}$)+L(n803nm$^{N2}$/f803nm$^{D2}$)$^{-1}$+M(n803nm$^{N2}$/f803nm$^{D2}$)$^{-2}$+O(n805nm$^{N3}$/f802nm$^{D2}$)$^{3}$+P(n805nm$^{N3}$/

$f802nm^{D3})^2+Q(n805nm^{N3}/f802nm^{D3})+R(n805nm^{N3}/f802nm^{D3})^{-1}+S(n805nm^{N3}/f802nm^{D3})^{-2}+U(n810nm^{N4}/f803nm^{D4})^3+V(n810nm^{N4}/f803nm^{D4})^2+W(n810nm^{N4}/f803nm^{D4})+X(n810nm^{N4}/f803nm^{D4})^{-1}+Y(n810nm^{N4}/f803nm^{D4})^{-2}+FF(n760nm/n815nm)^3+GG(n760nm/n815nm)^2+HH(n760nm/n815nm)+II$ wherein A to II, N1 to N4, and D1 to D4 are constants established independently for Hct and Hgb by non-linear multi-variable regression analysis and "n" designates the normalized intensity of light received by the near sensor at the respective wavelength and "f" designates the normalized intensity of light received by the far sensor at the respective wavelength.

Arithmetic circuit 25 provides the results of these calculations as output 24. Preferably, the values generated by the arithmetic circuit 25 are displayed on numeric display 20. In a most preferred embodiment, the user selects alternatively whether Hct or Hgb will be calculated and displayed.

A one-point calibration can also be performed on the monitor in order to adjust the output to equal that of a laboratory instrument and thus, increase the accuracy of the displayed measurement. To perform a one-point calibration the user draws a blood sample from the extracorporeal circuit while substantially simultaneously storing the values for the parameters being measured by the monitor. The user then measures the parameters on a separate apparatus and inputs the values into the monitor. The separate apparatus is preferably a laboratory instrument or other suitably accurate apparatus. The monitor's software adjusts the parameter values by adding or subtracting an offset value, based on the difference between apparatus and monitor values.

Figure 6:
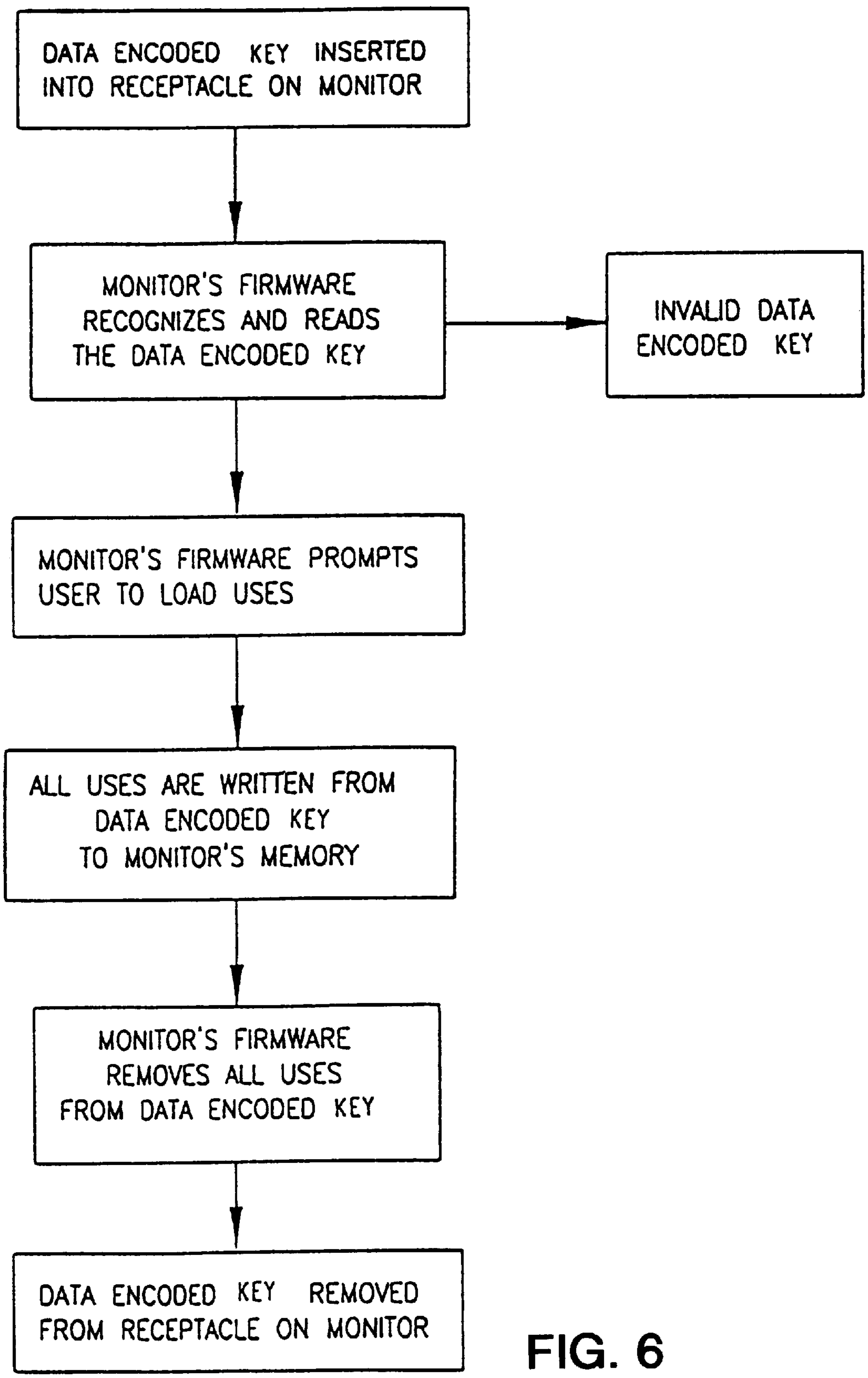
FIG. 6 is a block diagram showing the method of operation of the key reader.

The monitor can be further provided with an apparatus for regulating the number of uses. Preferably, the apparatus comprises a data encoded key, a receptacle on the monitor for receiving and reading the key, and firmware recognizing the encoded data. In operation, the electronic key encoded with erasable data recognized by the firmware as a number of uses. The key is inserted into the receptacle and the firmware reads the data encoded on the key. The firmware then prompts the user to load all or a lesser number of uses. The total number of uses loaded by the user is subtracted from the key and loaded into the monitor. Each time the monitor is used the arithmetic circuit reduces the number of uses left on the monitor by one. A use is defined by the manufacturer. In a most preferred embodiment, the use comprises continuous operation for eight hours or removal from the conduit for a set period of time. A suitable method for such regulation is shown diagramatically in FIG. 6.

We claim:

1. An apparatus for measuring blood parameters through conduit of an extracorporeal circuit, comprising:

- a light source which transmits light at a plurality of wavelengths to the conduit;
- a near sensor which senses light at a plurality of wavelengths connected to receive light a first distance from the light source which has been one of reflected and transmitted by the blood, wherein signals generated by the near sensor are indicative of the intensity of the sensed light at a plurality of wavelengths;
- a far sensor which senses light at a plurality of wavelengths connected to receive light a second distance from the light source which has been one of reflected and transmitted by the blood, wherein signals generated by the far sensor are indicative of the intensity of light at a plurality of wavelengths; and
- an arithmetic circuit connected to receive the signals from the near sensor and the far sensor and wherein the signals are used to calculate a parameter of blood and to generate an output signal indicative thereof.

2. An apparatus as in claim 1, wherein the blood parameters are at least one of oxygen saturation, hematocrit and hemoglobin concentration.

3. An apparatus as in claim 1, wherein the light source emits wavelengths between 450 nm and 1150 nm.

4. An apparatus as in claim 1, wherein the light source is a tungsten halogen bulb.

5. An apparatus as in claim 1, wherein the near sensor is a first charge coupled device and the far sensor is a second charge coupled device of a single two-channel spectrometer.

6. An apparatus as in claim 1, wherein the near sensor is a first spectrometer and the far sensor is a second spectrometer.

7. An apparatus as in claim 1, wherein the blood parameter being measured is oxygen saturation and wherein the arithmetic circuit derives the blood oxygen saturation from the ratios of reflected light at wavelengths between 660 nm and 815 nm in accordance with the formula:

$$\text{oxygen saturation}=A(n680nm/n815nm)^3+B(n680nm/n815nm)^2+C(n680nm/n815nm)+D(n680nm/n815nm)^{-1}+E(n680nm/n815nm)^{-2}+F(n710nm/n740nm)^3+G(n710nm/n740nm)^2+H(n710nm/n740nm)+I(n710nm/n740nm)^{-1}+J(n710nm/n740nm)^{-2}+L(n760nm/n815nm)^3+M(n760nm/n815nm)^2+N(n760nm/n815nm)+O(n760nm/n815nm)^{-1}+P(n760nm/n815nm)^{-2}+T(f680nm/f815nm)^3+U(f680nm/f815nm)^2+V(f680nm/f815nm)+W(f680nm/f815nm)^{-1}+X(f680nm/f815nm)^{-2}+Y(f710nm/f740nm)^3+Z(f710nm/f740nm)^2+AA(f710nm/f740nm)+BB(f710nm/f740nm)^{-1}+CC(f710nm/f740nm)^{-2}+DD(f760nm/f815nm)^3+EE(f760nm/f815nm)^2+FF(f760nm/f815nm)+GG(f760nm/f815nm)^{-1}+HH(f760nm/f815nm)^{-2}+II(n815nm/f810nm)^3+JJ(n815nm/f810nm)^2+KK(n815nm/f810nm)+LL$$

wherein A to GG are constants, n designates the reflectance detected by the near sensor, and f designates the reflectance detected by the far sensor.

8. An apparatus as in claim 1, wherein the blood parameter being measured is one of hemoglobin concentration and hematocrit and wherein the arithmetic circuit derives one of hemoglobin concentration and hematocrit from the ratios of reflected light at a plurality of wavelengths between 760 nm and 999 nm in accordance with the formula:

$$\text{hemoglobin and hematocrit}=A(n815nm/f810nm)^3+B(n815nm/f810nm)^2+C(n815nm/f810nm)+D(n815nm/f810nm)^{-1}+E(n815nm/f810nm)^{-2}+F(n850nm/f825nm)^3+G(n850nm/n825nm)^2+H(n850nm/f825nm)+I(n850nm/f825nm)^{-1}+J(n850nm/f825nm)^{-2}+O(n880nm/f827nm)^3+P(n880nm/f827nm)^2+Q(n880nm/f827nm)+R(n880nm/f827nm)^{-1}+S(n880nm/f827nm)^{-2}+U(n900nm/f830nm)^3+V(n900nm/f830nm)^2+W(n900nm/f830nm)+X(n900nm/f830nm)^{-1}+Y(n900nm/F830nm)^{-2}+Z(n999nm/f935nm)^3+AA(n999nm/f935nm)^2+BB(n999nm/f935nm)+CC(n999nm/f935nm)^{-1}+DD(n999nm/f935nm)^{-2}+EE(n760nm/n815nm)^3+FF(n760nm/n815nm)^2+GG(n760nm/n815nm)+HH$$

when blood hemoglobin concentration is less than 9 or hematocrit is less than 25, and hemoglobin and hematocrit= $A(n802nm^{N1}/f802nm^{D1})^3+B(n802nm^{N1}/f802nm^{D1})^2+C(n802nm^{N1}/f802nm^{D1})+D(n802nm^{N1}/f802nm^{D1})^{-1}+E(n802nm^{N1}/f802nm^{D1})^{-2}+I(n803nm^{N2}/f803nm^{D2})^3+J(n803nm^{N2}f803nm^{D2})^2+K(n803nm^{N2}/f803nm^{D2})+L(n803nm^{N2}/f803nm^{D2})^{-1}+M(n803nm^{N2}/f803nm^{D2})^{-2}+O(n805nm^{N3}/f802nm^{D2})^3+P(n805nm^{N3}/f802nm^{D3})^2+Q$ $(n805nm^{N3}/f802nm^{D3})+R(n805nm^{N3}/f802nm^{D3})^{-1}+S(n805nm^{N3}/f802nm^{D3})^{-2}+U(n810nm^{N4}/f803nm^{D4})^{3}+V(n810nm^{N4}/f803nm^{D4})^{2}+W(n810nm^{N4}/f803nm^{D4})+X(n810nm^{N4}f803nm^{D4})^{-1}+Y(n810nm^{N4}/f803nm^{D4})^{-2}+FF(n760nm/n815nm)^{3}+GG(n760nm/n815nm)^{2}+HH(n760nm/n815nm)+II$ when blood hemoglobin concentration is greater than or equal to 9 or hematocrit is greater than or equal to 25 and wherein A to II are constants, n designates the reflectance sensed by the near sensor, and f designates the reflectance sensed by the far sensor.

9. An apparatus as in claim 1, further comprising a source optical fiber connected to transmit light to the conduit from the light source, the source optical fiber having a first end connected to the light source and a second terminal end connected adjacent the conduit, the near sensor receives light from a near optical fiber, the near optical fiber having a first end connected to the near sensor and a second terminal end connected adjacent the conduit, and the far sensor receives light from a far optical fiber, the far optical fiber having a first end connected to the far sensor and a second terminal end connected adjacent the conduit.

10. An apparatus as in claim 9, further comprising a clamp for mounting a terminal end of the source optical fiber, a terminal end of the near optical fiber and a terminal end of the far optical fiber such that the source fiber, the near optical fiber and the far optical fiber are in optical communication with the conduit of the extracorporeal circuit.

11. An apparatus as in claim 9, wherein a terminal end of the near optical fiber is positioned about 0.8 mm from a terminal end of the source optical fiber and a terminal end of the far optical fiber is positioned about 1.2 mm from the terminal end of source optical fiber.

12. An apparatus as in claim 9, wherein a terminal end of the near optical fiber, a terminal end of the far optical fiber and a terminal end of the source optical fiber are positioned co-axially along the flow path of blood in the conduit.

13. An apparatus as in claim 10, wherein the clamp secures the terminal ends of the optical fibers so as to bias the terminal ends of the optical fibers against the conduit.

14. An apparatus for measuring blood parameters through conduit of an extracorporeal circuit, comprising:

means for emitting light at a plurality of wavelengths into blood flowing through the conduit;

near means for receiving light reflected from the blood;

far means for receiving light reflected from the blood, wherein the far receiving means and near receiving means are connected to receive reflected light at positions which are differentially spaced from the point where light is emitted into the conduit;

means for generating signals indicative of the intensity at a plurality of wavelengths of light received at a plurality of wavelengths by the near receiving means and far receiving means; and means for calculating receiving the signals from the signal generating means wherein, the calculating means calculates blood parameters and generates an output signal indicative thereof.

15. An apparatus as in claim 14, wherein the blood parameters are at least one of oxygen saturation, hematocrit and hemoglobin concentration.

16. A method for measuring a parameter of blood passing through conduit in an extracorporeal circuit with a blood monitor having a light source, a near sensor and a far sensor, the method comprising:

directing a plurality of wavelengths from the light source through the conduit into the blood;

directing light reflected by the blood through the conduit to the near sensor;

directing light reflected by the blood through the conduit to the far sensor;

measuring the light reflected by the blood to the near sensor and the far sensor at a plurality of wavelengths; and calculating the blood parameter using the quantity of reflected light detected at a plurality of wavelengths by the near sensor and the far sensor.

17. A method as in claim 16, wherein the blood parameter is at least one of oxygen saturation, hemoglobin concentration and hematocrit.

18. A method for measuring blood parameters through a conduit, comprising:

providing a blood monitor including a near sensor, a far sensor and a light source which are connected by optical fibers to a clamp;

mounting the clamp on the conduit in a manner such that terminal ends of the optical fibers are held against the outer surface of the conduit;

emitting light at a plurality of wavelengths through the conduit into the blood;

receiving light at a plurality of wavelengths reflected by the blood;

quantitating the light reflected at the near sensor and the far sensor at a plurality of wavelengths; and calculating a blood parameter from the quantity of reflected light.

* * * * *